(12) United States Patent
Tal

(10) Patent No.: US 8,608,767 B2
(45) Date of Patent: Dec. 17, 2013

(54) VARICOSE VEIN DISSECTOR AND REMOVAL APPARATUS

(75) Inventor: Michael G. Tal, Woodbridge, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 13/188,092

(22) Filed: Jul. 21, 2011

(65) Prior Publication Data

US 2011/0301624 A1  Dec. 8, 2011

Related U.S. Application Data

(63) Continuation of application No. 11/884,200, filed as application No. PCT/US2006/006425 on Feb. 24, 2006, now Pat. No. 8,034,070.

(60) Provisional application No. 60/656,573, filed on Feb. 25, 2005.

(51) Int. Cl.
*A61B 17/34* (2006.01)
*B26B 11/00* (2006.01)

(52) U.S. Cl.
USPC ............................................ 606/185; 30/136

(58) Field of Classification Search
USPC ............ 606/167, 211, 222, 225, 148, 185, 606/190–195, 159; 30/162, 163, 286, 330, 30/339; 600/36, 127
See application file for complete search history.

(56) References Cited

U.S. PATENT DOCUMENTS

| | | | |
|---|---|---|---|
| 3,608,539 A | 9/1971 | Miller | |
| 5,758,665 A | 6/1998 | Suval | |
| 5,776,156 A | 7/1998 | Shikhman | |
| 5,868,711 A | 2/1999 | Kramer et al. | |
| 6,453,906 B1 | 9/2002 | Taylor et al. | |
| 7,308,896 B2 | 12/2007 | Cruz | |
| 8,034,070 B2 * | 10/2011 | Tal | 606/190 |
| 2005/0216048 A1 | 9/2005 | Suval et al. | |

FOREIGN PATENT DOCUMENTS

GB 2195542 4/1998

* cited by examiner

*Primary Examiner* — Tuan V Nguyen
(74) *Attorney, Agent, or Firm* — Welsh Flaxman & Gitler LLC

(57) ABSTRACT

A varicose vein dissector and removal apparatus includes a handle having a first end and a second end, a dissector extending from the first end of the handle and a hook extending from the second end of the handle, and a blade positioned within the dissector for movement between a use position and a storage position. The apparatus is used by creating an initial incision in skin over a varicose vein to be removed, advancing the dissector into the incision and dissecting around the varicose vein to be removed, pushing the dissector against an inner surface of the skin a predetermined distance from the initial incision, exposing the blade by moving it from its storage position to its use position and creating a second incision in the skin letting the dissector protrude out of the skin, and grasping the vein with the hook and removing the vein.

12 Claims, 7 Drawing Sheets

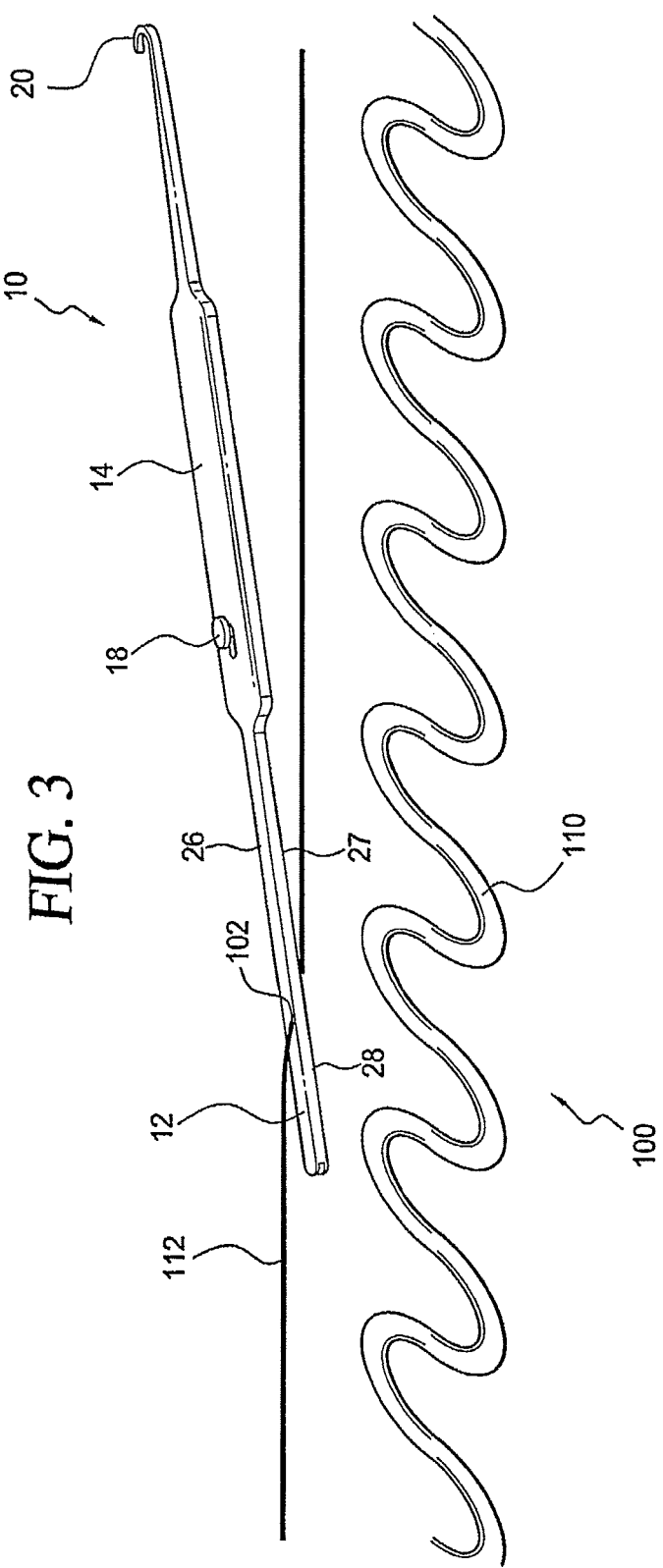

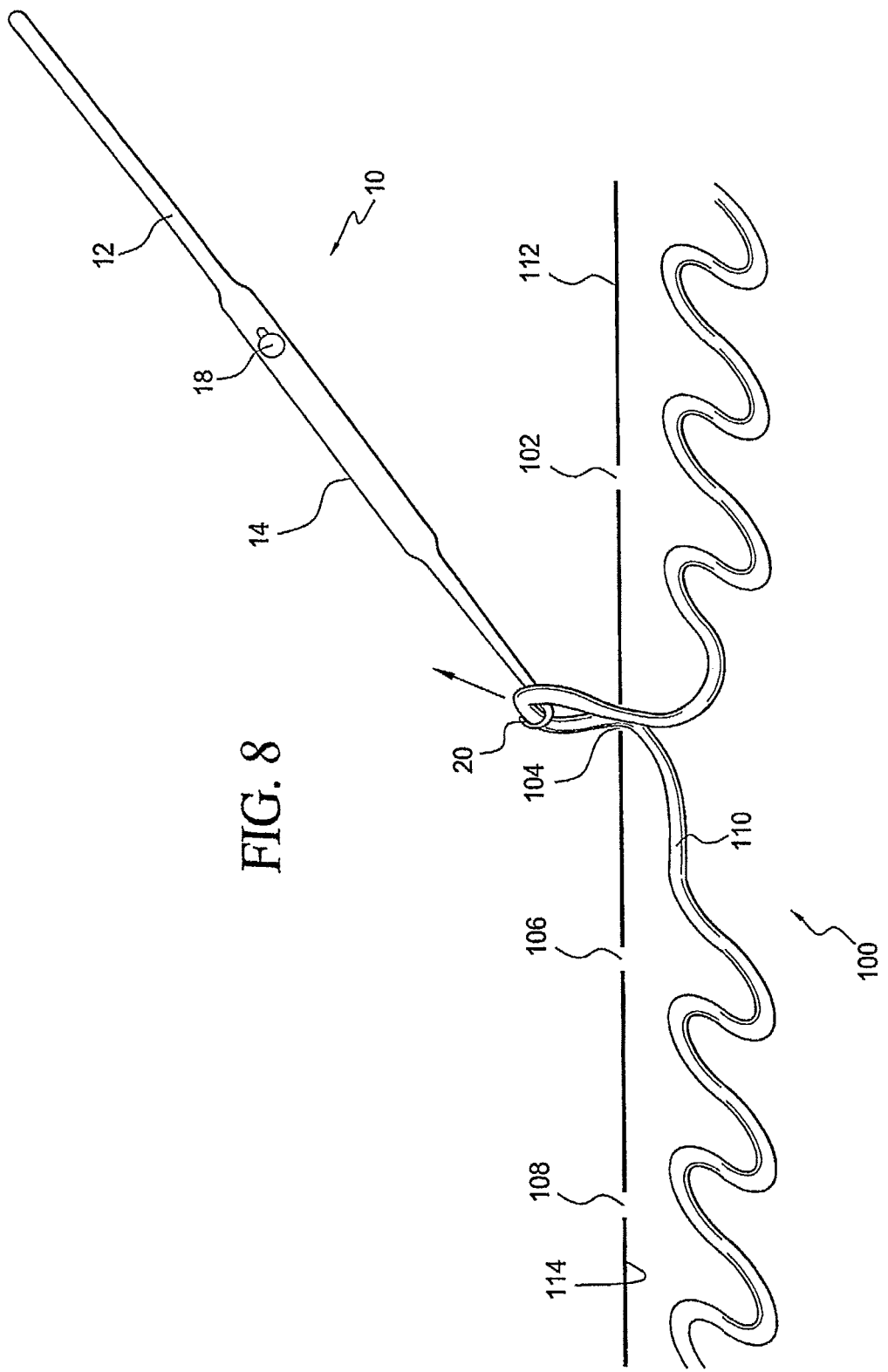

VARICOSE VEIN DISSECTOR AND REMOVAL APPARATUS

CROSS REFERENCE TO RELATED APPLICATION

The present application is a continuation of U.S. patent application Ser. No. 11/884,200, entitled "VARICOSE VEIN DISSECTOR AND REMOVAL APPARATUS", filed Aug. 13, 2007, which issued as U.S. Pat. No. 8,034,070, which is the National Stage of International Application No. PCT/US2006/006425, filed Feb. 24, 2006, entitled AVARICOSE VEIN DISSECTOR AND REMOVAL APPARATUS@, which claims the benefit of U.S. Provisional Patent Application Ser. No. 60/656,573, filed Feb. 25, 2005, entitled "VARICOSE VEIN DISSECTOR AND REMOVAL APPARATUS".

BACKGROUND OF THE INVENTION

1. Field of the Invention

The invention relates to a varicose vein dissector and removal apparatus. The present invention is also directed to a method for varicose vein removal utilizing the present apparatus.

2. Description of the Prior Art

Ten to fifteen percent of the population suffers from varicose veins. These veins have usually lost their ability to carry blood back to the heart and blood often accumulates in these veins. As a result, the veins may become swollen, distorted, and prominent. Inefficient or defective one-way valves that prevent blood from draining back through the vein usually cause this condition. Varicose veins may cause patients to experience various symptoms including aching, burning, swelling, cramping and itching. More serious complications of varicose veins can include thrombophlebitis, dermatitis, hemorrhage and ulcers. Many patients seek medical treatment of varicose veins for cosmetic reasons.

Several treatment options exist for the treatment of varicose veins. One option is sclerotherapy. In sclerotherapy, the affected veins are injected with a sclerosing solution. The sclerosing solution causes inflammation and sclerosis of the veins. The sclerosis results in localized scarring or closure of the veins. There are several complications associated with sclerotherapy including staining of the skin, ulcers, skin ischemia, necrosis and neuropathy.

Another procedure for treatment of varicose veins is ambulatory phlebectomy (also knows as stab phlebectomy or microphelebectomy). In this technique, incisions are made in the skin of the patient, and a hook is inserted into the incision to grip or hook the veins to be removed. When the veins are grabbed, the veins are gently pulled through the surgical incision and severed. This procedure usually requires an assistant to the surgeon and can take up to 1-2 hours in some cases. This procedure also usually requires multiple incisions in order to hook the affected veins. It is often difficult to completely remove the entire affected veins.

More particularly, the current technique for performing ambulatory phlebectomy is as follows: a small incision (1-2 mm) is made in the skin over the vein; the vein is dissected from its surrounding tissue (optional); a hook is used to grab the vein through the small incision and pull the vein partly out of the skin; a clamp is used to gently and meticulously pull the vein out of the skin (the vein usually severs at the skin after several centimeters of vein have been removed); and another incision is made several centimeters away and the process is repeated.

As described above, traditional ambulatory phlebectomy is performed using individual small punctures or incisions over superficial varicose veins followed by grasping of the veins and teasing them out of the skin. Included among the drawbacks to this technique are that the amount of vein removed is sometimes small, the veins are pulled and torn easily causing bleeding and hematoma, many punctures or incisions are often required, the procedure is time consuming, and there are often areas of vein that are not removed.

As those skilled in the art will certainly appreciate, a need exists for an improved technique for performing ambulatory phlebectomy, as well as improved surgical apparatuses. The present invention provides both an improved surgical technique and an associate surgical apparatus.

SUMMARY OF THE INVENTION

It is, therefore, an object of the present invention to provide a varicose vein dissector and removal apparatus. The apparatus includes a handle having a first end and a second end, a dissector extending from the first end of the handle and a hook extending from the second end of the handle, and a blade positioned within the dissector for movement between a use position and a storage position.

It is also an object of the present invention to provide an apparatus wherein the handle, hook and dissector are made from a stiff plastic material or metal.

It is another object of the present invention to provide an apparatus wherein the dissector is substantially flat.

It is a further object of the present invention to provide an apparatus wherein the dissector includes parallel upper and lower surfaces.

It is also another object of the present invention to provide an apparatus wherein the dissector has a length of approximately 5 cm to approximately 7 cm.

It is yet another object of the present invention to provide an apparatus wherein the dissector has a width of approximately 3 mm and a thickness of slightly over 1 mm.

It is also a further object of the present invention to provide an apparatus wherein the dissector includes a free end from which the blade is selectively extended when moved between a use position and a storage position.

It is still a further object of the present invention to provide an apparatus wherein a button is coupled to the blade facilitating movement between a use position and storage position.

It is also an object of the present invention to provide an apparatus wherein the button extends up through a slot formed in the handle.

It is another object of the present invention to provide an apparatus wherein the hook is substantially U-shaped.

It is a further object of the present invention to provide an apparatus wherein the hook is approximately 2 mm to approximately 5 mm in diameter.

It is also an object of the present invention to provide a method for ambulatory phlebectomy employing the present varicose vein dissector and removal apparatus. The method is achieved by creating an initial incision in skin over a varicose vein to be removed, advancing the dissector into the incision and dissecting around the varicose vein to be removed, pushing the dissector against an inner surface of the skin a predetermined distance from the initial incision, exposing the blade by moving it from its storage position to its use position and creating a second incision in the skin letting the dissector protrude out of the skin, and grasping the vein with the hook and removing the vein.

It is another object of the present invention to provide a method wherein the step of pushing is performed several centimeters from the initial incision.

It is still a further object of the present invention to provide an apparatus including the step of repeating the steps of advancing, pushing and exposing along the length of the varicose vein.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 3 to 8 show the steps associated with the use of the present apparatus in performing ambulatory phlebectomy.

DESCRIPTION OF THE PREFERRED EMBODIMENTS

Figure 1:
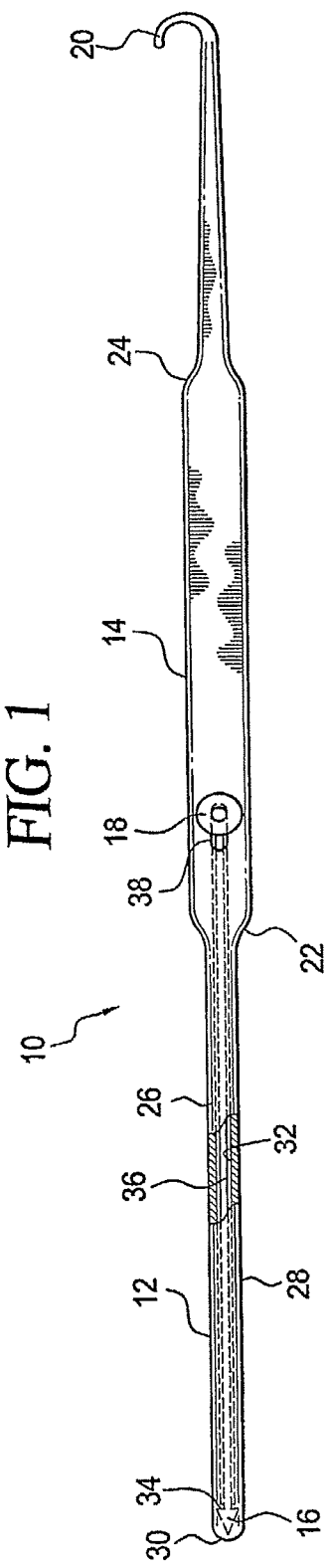
FIG. 1 is a top plan view of the present a varicose vein dissector and removal apparatus with the internal components shown in phantom and the blade in its storage positioned.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various figures, a varicose vein dissector and removal apparatus 10 for performing an ambulatory phlebectomy is disclosed. Briefly, the present apparatus 10 includes an elongated stiff component, that is, a dissector 12, connected to a handle 14. A blade 16 is positioned within the dissector 12 for selective movement between a use position extending from the dissector 12 and a storage position hidden within the dissector 12. The blade 16 is connected to a button 18 extending from the handle 14 for ready actuation by a user to move the blade 16 between its storage position and its use position. After the dissection of a varicose vein in a manner discussed below in greater detail, the blade 16 is pushed forward to its use position using the button 18 and the blade 16 is forced through the skin creating an incision in the skin from the inside out. The back end of the apparatus 10 includes a hook 20 shaped and dimensioned for grasping of the vein and pulling of the vein out through the skin. With the foregoing in mind and as will be appreciated based upon the following detailed disclosure, an operator will have control over the activation of the present apparatus 10 and the timing of the blade 16 exposure.

More particularly, the present apparatus 10 includes a centrally positioned handle 14 having a first end 22 and a second end 24. A dissector 12 extends from the first end 22 of the handle 14 and a hook 20 extends from the second end 24 of the handle 14. In accordance with a preferred embodiment, the handle 14, hook 20 and dissector 12 are made from a stiff plastic material or metal. The present apparatus 10 must be stiff enough to dissect tissue but the edges of it should be blunt to prevent damage to the veins during dissection.

Figure 2:
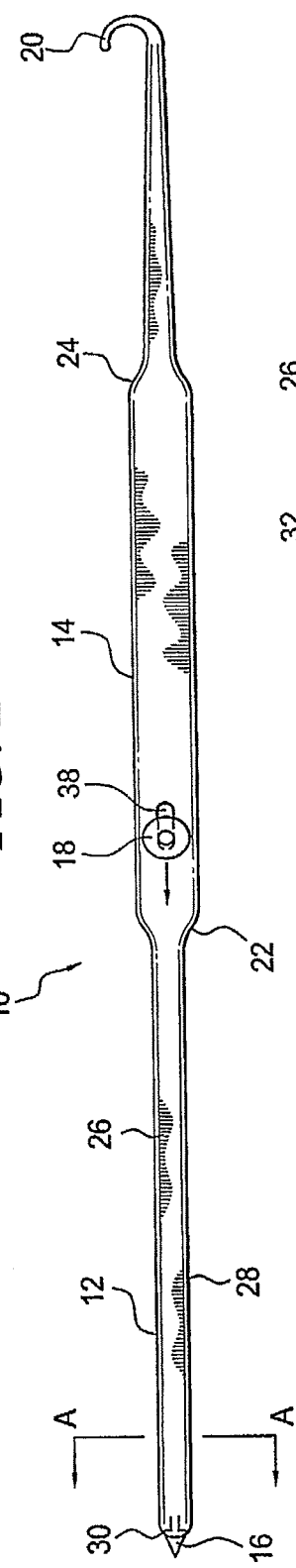
FIG. 2 is a top plan view of the present apparatus with the blade in its use position.
Figure 2A:
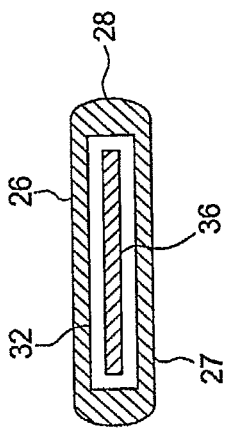
FIG. 2A is a cross sectional view along the line A-A in FIG. 2.
Figure 4:
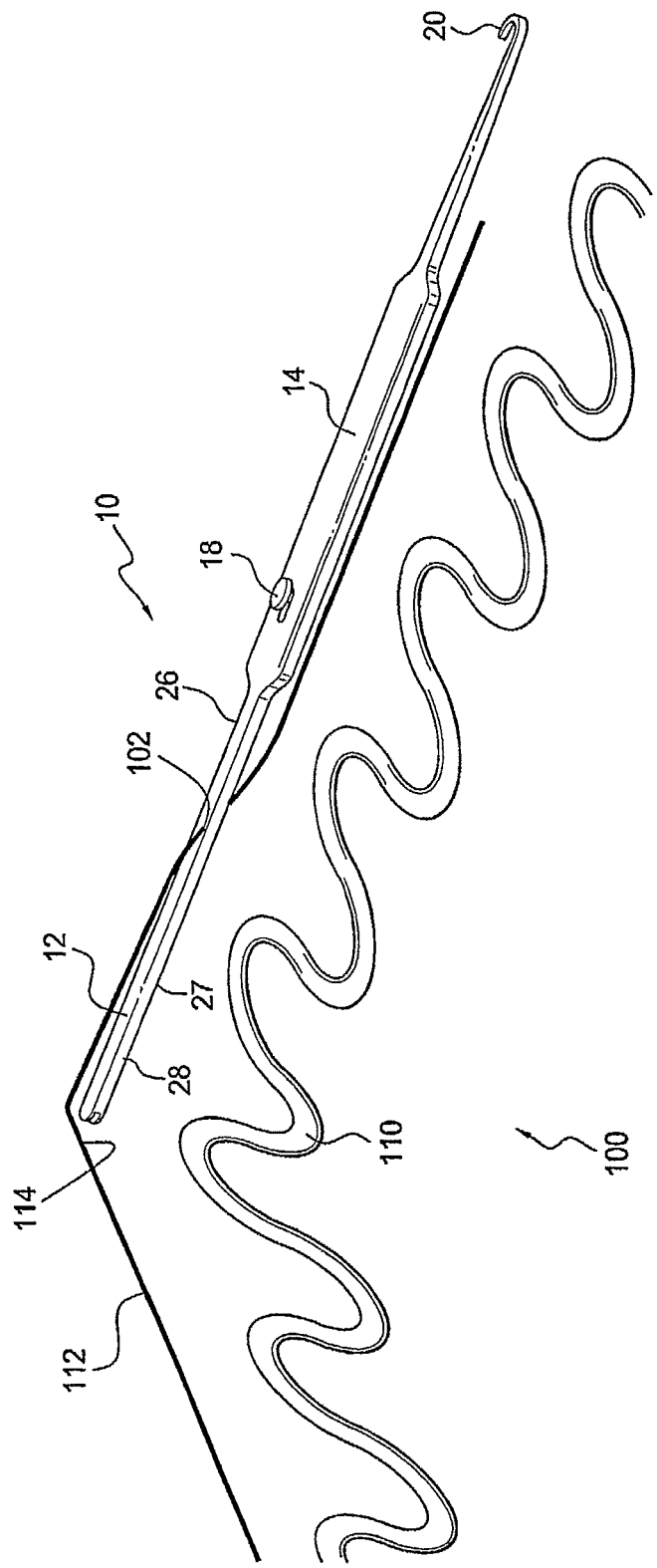

As will be appreciated based upon the following disclosure, the dissector 12 is shaped and dimensioned for passage through an initial small incision made in the skin measuring anywhere from 1 mm to 5 mm, dissection around a varicosity and placement against the internal surface of the skin several centimeters from the initial incision. In accordance with a preferred embodiment, the dissector 12 is substantially flat including parallel upper and lower surfaces 26, 27 with a rounded edge 28 connecting the upper and lower surfaces 26, 27. With this in mind, the dissector 12 has a length of approximately 5 cm to approximately 7 cm. The dissector 12 preferably has a width of approximately 3 mm and a thickness of slightly over 1 mm. In fact, the dissector 12 has a width that is less than a width of the handle 14 (see FIGS. 1 and 2). Although the dissector is flat in shape in accordance with a preferred embodiment of the present invention, the dissector may be constructed with a variety of cross sectional profiles without departing from the spirit of the present invention.

The dissector 12 is provided with a free end 30 from which the blade 16 is selectively extended for creating additional incisions in accordance with the present invention. More particularly, the dissector 12 is provided with a central passage 32 in which the blade 16 is stored. As will be appreciated further based upon the following disclosure of the procedure in accordance with the present invention, the small blade 16 is stored within the dissector 12 for reasons of safety and prevention of damage to the tissues and varicosities during dissection. In accordance with a preferred embodiment, the blade 16 is shaped and dimensioned to extend about a millimeter from the free end 30 of the dissector 12 when moved to its use position. In accordance with a preferred embodiment of the present invention, the portion of the blade 16 extending from the free end 30 of the dissector 12 is shaped like a standard blade with one side sharp or shaped like an arrow with sharp edges on both sides. As those skilled in the art will appreciate, various blade designs could be used without departing form the spirit of the present invention.

The rear end 34 of the blade 16 is coupled to an actuator 36 extending back through the dissector 12 to a button 18 that extends up through the handle 14 for actuation by the user. As such, a physician using the present apparatus 10 may readily actuate the button 18 to move the blade 16 from its storage position within the dissector 12 to its use position extending beyond the free end 30 of the dissector 12. With this in mind, the handle 14 is provided with a longitudinal slot 38 from which the button 18 extends. The slot 38 allows one to move the button 18 (and ultimately the actuator 36 and blade 16) forward and backward between a use position and a storage position.

As briefly mentioned above, a hook 20 extends from the second end 24 of the handle 14. The hook 20 is substantially U-shaped for grasping and retrieving veins as discussed below. In accordance with a preferred embodiment the hook 20 is approximately 2 mm to approximately 5 mm in diameter, depending upon the size of vein to be removed (bigger hooks are used for bigger veins). With this in mind, the present apparatus will be made with hooks of various sizes to be used in accommodating the needs of specific patient conditions.

The present apparatus 10 employs a modified phlebectomy technique in which dissection with a long dissector along the entire length of the varicosity 100 is performed prior to vein extraction (See FIGS. 3 to 8). After the initial puncture or incision 102 is made in the area of the varicose vein 100, the subsequent incisions 104, 106, 108 are made with the present apparatus 10, in particular, the dissector 12 and blade 16, several centimeters from the previous puncture site (See FIGS. 5, 6, 7 and 8).

As those skilled in the art will certainly appreciate, the terms puncture and, incision are generally interchangeable for the purposes of describing an ambulatory phlebectomy. Specifically, some operators use a needle to make the initial skin incision, in which case it is more a puncture hole, while others use a surgical blade, in which case it is more an incision. Since most physicians use a surgical blade, the term incision is predominantly used throughout the present disclosure, although those skilled in the art will appreciate that punctures certainly fall within the spirit of the present invention.

The incisions 102, 104, 106, 108 are formed repeatedly along the whole length of the varicosity 100. The dissector 12 can be inserted through one of the incision sites 102, 104, 106, 108 and the dissection procedure can be continued. After dissection and the creation of a series of incisions 102, 104, 106, 108 along the varicosity 100, the vein 110 is grasped using the hook 20 extending from the second end 24 of the present apparatus 10 and removed easily. The amount of vein 110 removed and the cosmetic results after vein removal using the present continuous phlebectomy technique are superior to traditional phlebectomy.

Figure 5:
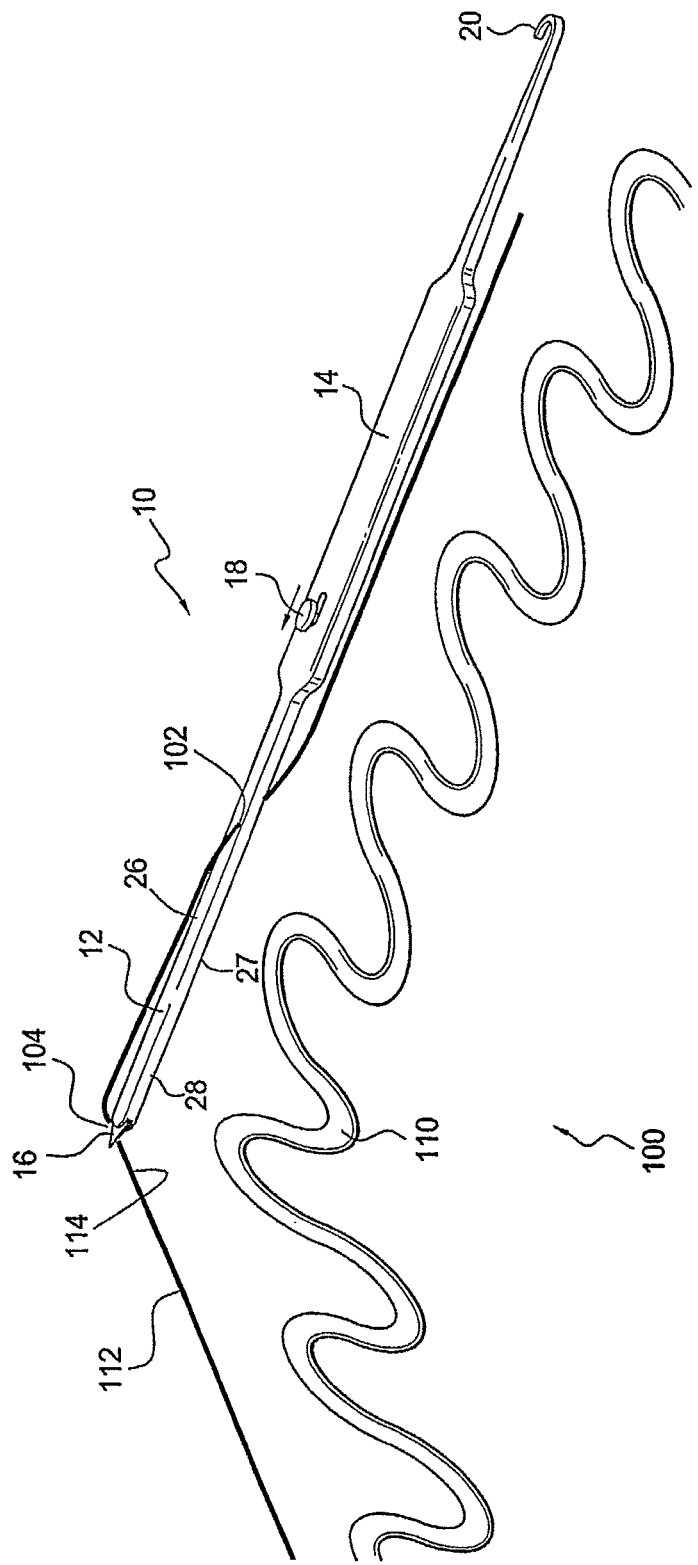
Figure 6:
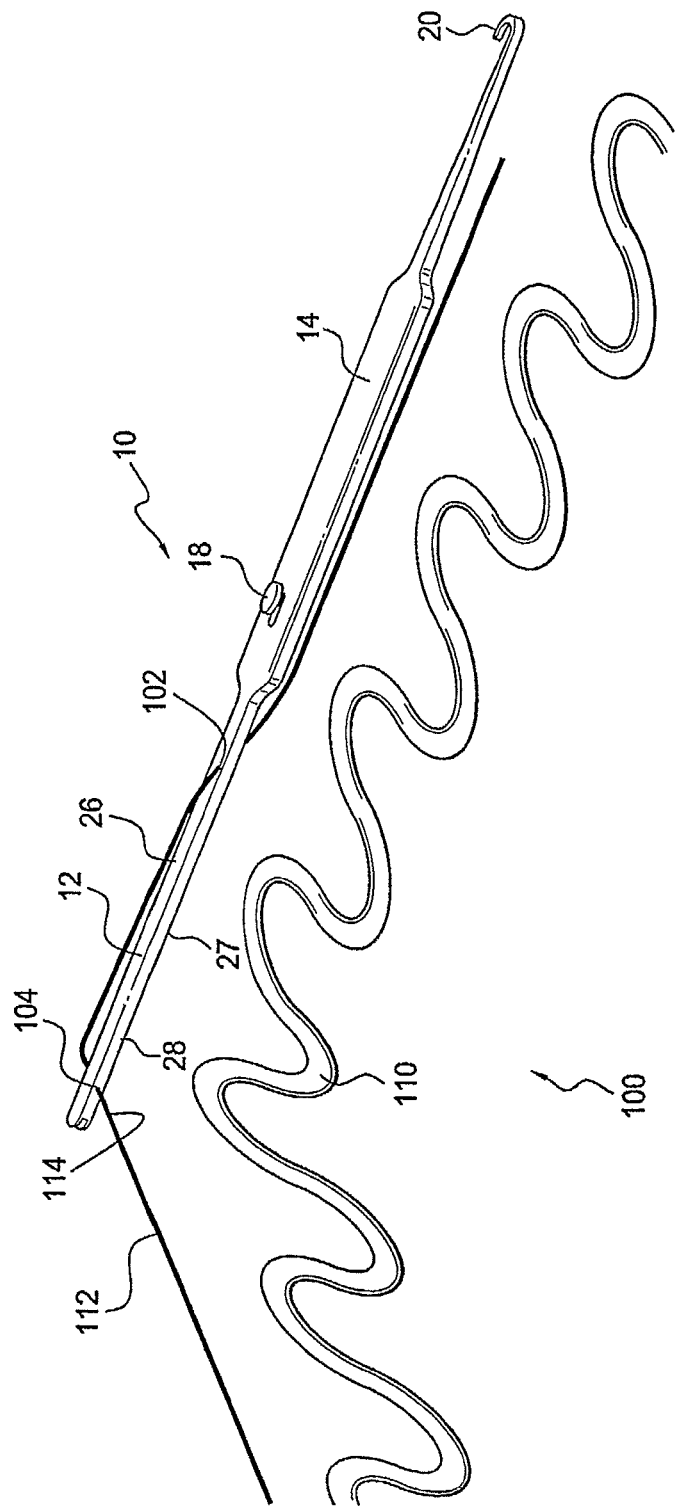
Figure 7:
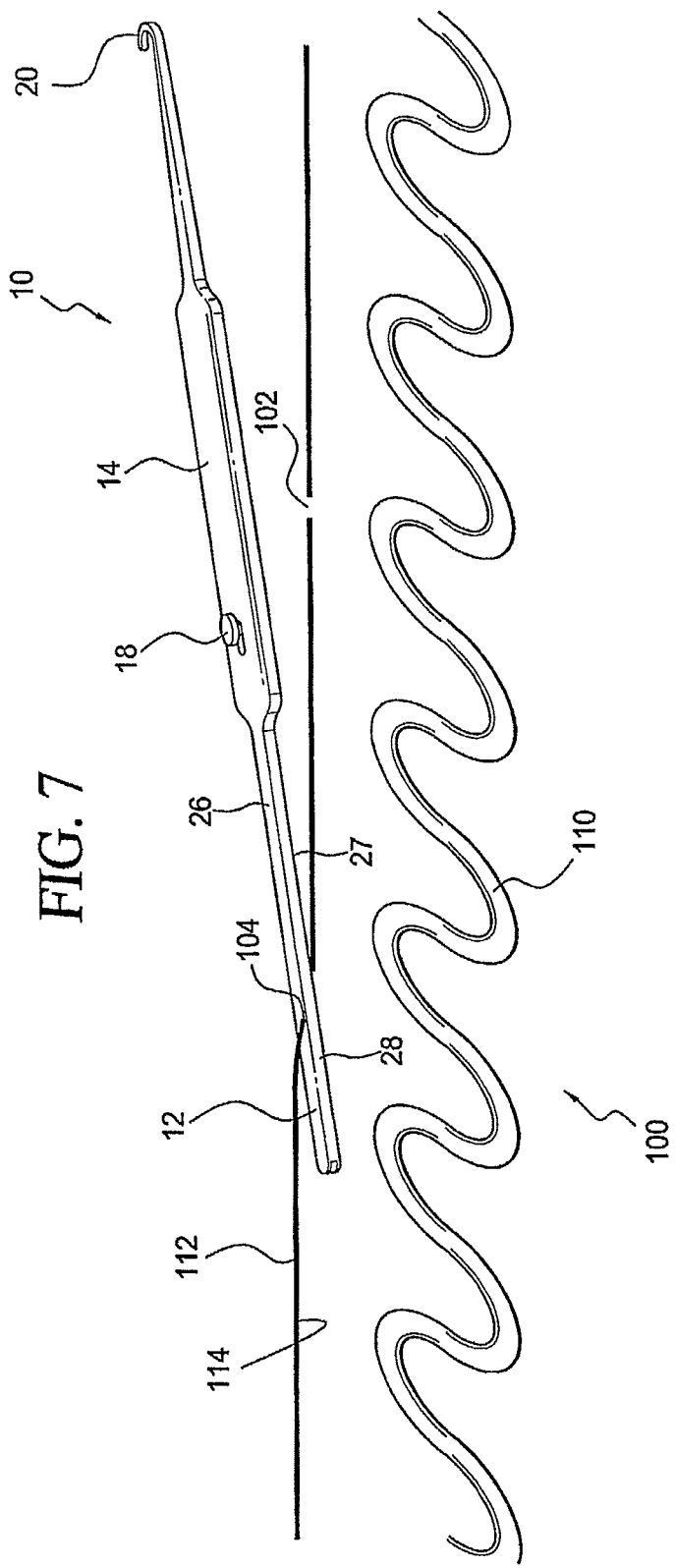

More particularly, an initial small incision (1-2 mm) 102 is made in the skin 112 over the vein 110 to be removed, the dissector 12 is advanced into the incision 102 and dissection around the varicosity 100 is performed (FIG. 3). The dissector 12 is pushed against the inner surface 114 of the skin 112 several centimeters from the initial incision 102 (FIG. 4) and the blade 16 is exposed by moving the button 18 forward such that the blade 16 is moved from its storage position to its use position (FIG. 5). This creates an incision 104 in the skin 112 and lets the dissector 12 protrude out of the skin 112 (FIG. 6). The blade 16 in the dissector 12 is then withdrawn back to its storage position within the dissector 12 and the dissector 12 is withdrawn from the initial incision 102. The dissector 12 is then advanced into the newly formed incision site and the process is repeated creating additional incisions 106, 108 and dissecting the vein 110 (FIG. 7). After all the varicosity 100 has been dissected, the hook 20 of the apparatus 10 is used to grasp the vein 110 and remove it (FIG. 8).

The present apparatus offers a variety of advantages. In particular, it provides enhanced efficiency as longer segments of vein will be pulled through each incision and the procedure time will, therefore, be reduced. The present device also offers improved safety by decreasing the number of required incisions, thereby reducing infection risk. The device further decreases the risk to the operator because the incision is made with the dissection device and not with an exposed blade. The present device is also cost-effective in that procedure time is reduced and the device is disposable (also providing reduced risk of infection to the patient).

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A varicose vein dissector and removal apparatus, comprising:
    a handle including a first end and a second end;
    a dissector extending from the first end of the handle and a hook extending from the second end of the handle, the dissector includes a central passage and has a length of approximately 5 cm to approximately 7 cm, and the dissector has a width that is less than a width of the handle;
    a blade positioned within the central passage of the dissector for movement between a use position where the blade is extended from a free end of the dissector and a storage position where the blade is stored within the central passage, a rear end of the blade is coupled to an actuator extending back through the central passage of the dissector to a button that extends up through a slot formed in the handle for actuation by the user.

2. The apparatus according to claim 1, wherein the handle, hook and dissector are made from a stiff plastic material or metal.

3. The apparatus according to claim 1, wherein the dissector is substantially flat.

4. The apparatus according to claim 3, wherein the dissector includes parallel upper and lower surfaces.

5. The apparatus according to claim 3, wherein the dissector has a width of approximately 3 mm and a thickness of slightly over 1 mm.

6. The apparatus according to claim 3, wherein the dissector includes a free end from which the blade is selectively extended when moved between a use position and a storage position.

7. The apparatus according to claim 1, wherein the dissector has a width of approximately 3 mm and a thickness of slightly over 1 mm.

8. The apparatus according to claim 1, wherein the dissector includes a free end from which the blade is selectively extended when moved between a use position and a storage position.

9. The apparatus according to claim 1, wherein the hook is substantially U-shaped.

10. The apparatus according to claim 9, wherein the hook is approximately 2 mm to approximately 5 mm in diameter.

11. The apparatus according to claim 10, wherein the dissector is substantially flat.

12. The apparatus according to claim 11, wherein the dissector includes parallel upper and lower surfaces.

* * * * *